(12) United States Patent
Ohashi et al.

(10) Patent No.: US 9,237,974 B2
(45) Date of Patent: Jan. 19, 2016

(54) DISPOSABLE DIAPER HAVING EXCELLENT MIGRATION SPEED AND SATISFACTORY FEELING

(75) Inventors: Naoto Ohashi, Kanonji (JP); Toshiya Yago, Kanonji (JP)

(73) Assignee: UNICHARM CORPORATION, Ehime (JP)

( * ) Notice: Subject to any disclaimer, the term of this patent is extended or adjusted under 35 U.S.C. 154(b) by 316 days.

(21) Appl. No.: 13/824,519

(22) PCT Filed: Sep. 26, 2011

(86) PCT No.: PCT/JP2011/072704
§ 371 (c)(1),
(2), (4) Date: Mar. 18, 2013

(87) PCT Pub. No.: WO2012/043843
PCT Pub. Date: Apr. 5, 2012

(65) Prior Publication Data
US 2013/0178815 A1    Jul. 11, 2013

(30) Foreign Application Priority Data

Sep. 30, 2010  (JP) .................................. 2010-223115

(51) Int. Cl.

| | | |
|---|---|---|
| *A61F 13/15* | (2006.01) | |
| *A61F 13/20* | (2006.01) | |
| *A61F 13/511* | (2006.01) | |
| *A61F 13/49* | (2006.01) | |
| *A61F 13/514* | (2006.01) | |
| *A61F 13/53* | (2006.01) | |

(52) U.S. Cl.
CPC ............ *A61F 13/51108* (2013.01); *A61F 13/49* (2013.01); *A61F 13/514* (2013.01); *A61F 13/53* (2013.01)

(58) Field of Classification Search
CPC combination set(s) only.
See application file for complete search history.

(56) References Cited

U.S. PATENT DOCUMENTS

| | | | |
|---|---|---|---|
| 6,171,682 B1 | 1/2001 | Raidel et al. | |
| 6,436,081 B1 * | 8/2002 | Wada et al. | ............... 604/385.01 |
| 8,450,556 B2 * | 5/2013 | Miyamoto et al. | ............ 604/380 |
| 8,865,965 B2 * | 10/2014 | Sato et al. | ...................... 604/380 |

(Continued)

FOREIGN PATENT DOCUMENTS

| | | |
|---|---|---|
| DE | 4422956 A1 | 1/1996 |
| EP | 2153983 A1 | 2/2010 |

(Continued)

OTHER PUBLICATIONS

International Search Report corresponding to PCT/JP2011/072704 dated Nov. 15, 2011.

*Primary Examiner* — Michele M Kidwell
(74) *Attorney, Agent, or Firm* — Hauptman Ham, LLP (57) ABSTRACT

A disposable diaper includes a liquid-permeable top sheet, a liquid-impermeable back sheet and an absorber between the top sheet and back sheet, and having a front body waist region, a crotch region and a back body waist region. The top sheet is a nonwoven fabric having on the skin contact surface a plurality of ridges and a plurality of recesses extending in the lengthwise direction of the disposable diaper, and alternating in the widthwise direction perpendicular to the lengthwise direction. The top sheet has point-like compressed sections at a prescribed density in the front body waist region and/or back body waist region, the ridges in prescribed zones having different heights than the adjacent ridges at the same location in the lengthwise direction.

21 Claims, 7 Drawing Sheets

(56) References Cited

U.S. PATENT DOCUMENTS

| | | |
|---|---|---|
| 2002/0058128 A1* | 5/2002 | Toyoshima et al. ............ 428/182 |
| 2005/0124951 A1* | 6/2005 | Kudo et al. .................... 604/380 |
| 2006/0276767 A1* | 12/2006 | Ueminami et al. ...... 604/385.31 |
| 2007/0298671 A1 | 12/2007 | Noda et al. |
| 2008/0085399 A1 | 4/2008 | Noda et al. |
| 2008/0119810 A1* | 5/2008 | Kuroda et al. ................. 604/379 |
| 2010/0178456 A1* | 7/2010 | Kuroda et al. ................. 428/136 |
| 2010/0249740 A1 | 9/2010 | Miyamoto et al. |
| 2011/0130737 A1* | 6/2011 | Sagisaka et al. .............. 604/380 |
| 2011/0144605 A1* | 6/2011 | Noda et al. .................... 604/361 |
| 2012/0089106 A1* | 4/2012 | Komatsu et al. ............... 604/367 |
| 2012/0095424 A1* | 4/2012 | Komatsu et al. ............... 604/367 |

FOREIGN PATENT DOCUMENTS

| | | | |
|---|---|---|---|
| JP | 06126871 A | 5/1994 | |
| JP | 2004000466 A | 1/2004 | |
| JP | 2008025081 A | 2/2008 | |
| JP | 2008025082 A | 2/2008 | |
| JP | 2009201964 A | 9/2009 | |
| JP | 2010158488 A | 7/2010 | |
| WO | 2008/156075 A1 * | 12/2008 | .............. A61F 13/15 |
| WO | 2012/073514 A1 * | 6/2012 | .............. D04H 1/44 |

* cited by examiner

DISPOSABLE DIAPER HAVING EXCELLENT MIGRATION SPEED AND SATISFACTORY FEELING

RELATED APPLICATIONS

The present application is a National Phase of International Application Number PCT/JP2011/072704, filed Sep. 26, 2011, and claims priority from Japanese Application Number 2010-223115, filed Sep. 30, 2010.

TECHNICAL FIELD

The present invention (disclosure) relates to a disposable diaper.

BACKGROUND ART

Absorbent articles, such as disposable diapers, generally have a top sheet migration speed that allows smooth migration of excreta such as urine into the top sheet, as well as, in order to prevent skin troubles such as mustiness, itching and eruption (irritation), an absorber migration speed such that excreta that have migrated to the top sheet further migrate into the absorber.

These requirements are met by a variety of disclosed top sheets and absorbent articles comprising them.

PTL 1 describes a nonwoven fabric composed mainly of thermoplastic resin fiber having a basis weight of no greater than 30 g/m². The non-woven fabric comprises fiber bundles with interspersed bonding sections (or point bonding sections), in which the fibers are bonded together by heat, and pores interspersed over the entirety or a portion of the non-woven fabric which are formed by further separation of the fibers. The bonding sections are interspersed at a density of 6-4/cm², and the overall bonding area ratio of the bonding sections in the fiber bundles is 10-30%.

PTL 2 describes a surface sheet for an absorbent article, having a heat contracted heat-shrinkable section and a high densified section with minimized heat shrinkage.

CITATION LIST

Patent Literature

PTL 1 Japanese Unexamined Patent Publication No. 6-126871
PTL 2 Japanese Unexamined Patent Publication No. 2004-466

SUMMARY OF INVENTION

Technical Problem

The nonwoven fabric described in PTL 1 has low bulk, and therefore when it is used as a top sheet in an absorbent article, the distance between the top sheet and the absorber is reduced which is believed to be responsible for the faster absorber migration speed. However, the nonwoven fabric described in PTL 1 is not configured for an increased top sheet migration speed, and therefore the top sheet migration speed is thought to be insufficient.

Furthermore, the nonwoven fabric described in PTL 1 has a poor cushioning property due to its low bulk, while its high contact area ratio results in hardness that might be problematic in terms of feeling during wear.

In addition, when the surface sheet described in PTL 2 is used as the top sheet for a disposable diaper, both the heat-shrinkable section and the high densified section potentially might have an inferior top sheet migration speed. In addition, since the surface sheet described in PTL 2 is formed by heat shrinkage, it might have poor cushioning properties and a problematic feeling during wear.

Thus, conventional top sheets and absorbent articles comprising them might have had problems of top sheet migration speed and feeling during wear.

It is therefore an object of the present invention to provide a disposable diaper having excellent top sheet migration speed and absorber migration speed, as well as a satisfactory feeling during wear.

Solution to Problem

As a result of diligent research directed toward solving the problems described above, the present inventors have completed this invention upon finding that the aforementioned problems can be solved by a disposable diaper comprising a liquid-permeable top sheet, a liquid-impermeable back sheet and an absorber between the top sheet and back sheet, and having a front body waist region, a crotch region and a back body waist region, wherein the top sheet is a nonwoven fabric having on the skin contact surface a plurality of ridges and a plurality of recesses extending in the lengthwise direction of the disposable diaper, and alternating in the widthwise direction perpendicular to the lengthwise direction, the top sheet has point-like compressed sections, formed by compressing the ridges and/or recesses on the front body waist region and/or the back body waist region, at a density in the range of 4.0-7.0/cm², and zones of ridges having different heights are present in the front body waist region and/or the back body waist region, sandwiched by two point-like compressed sections, the ridges in those zones having different heights than the adjacent ridges at the same location in the lengthwise direction.

Advantageous Effects of Invention

The disposable diaper of the invention has excellent top sheet migration speed and absorber migration speed, as well as a satisfactory feeling during wear.

DESCRIPTION OF EMBODIMENTS

The disposable diaper of the invention will now be explained in detail.

Figure 1:
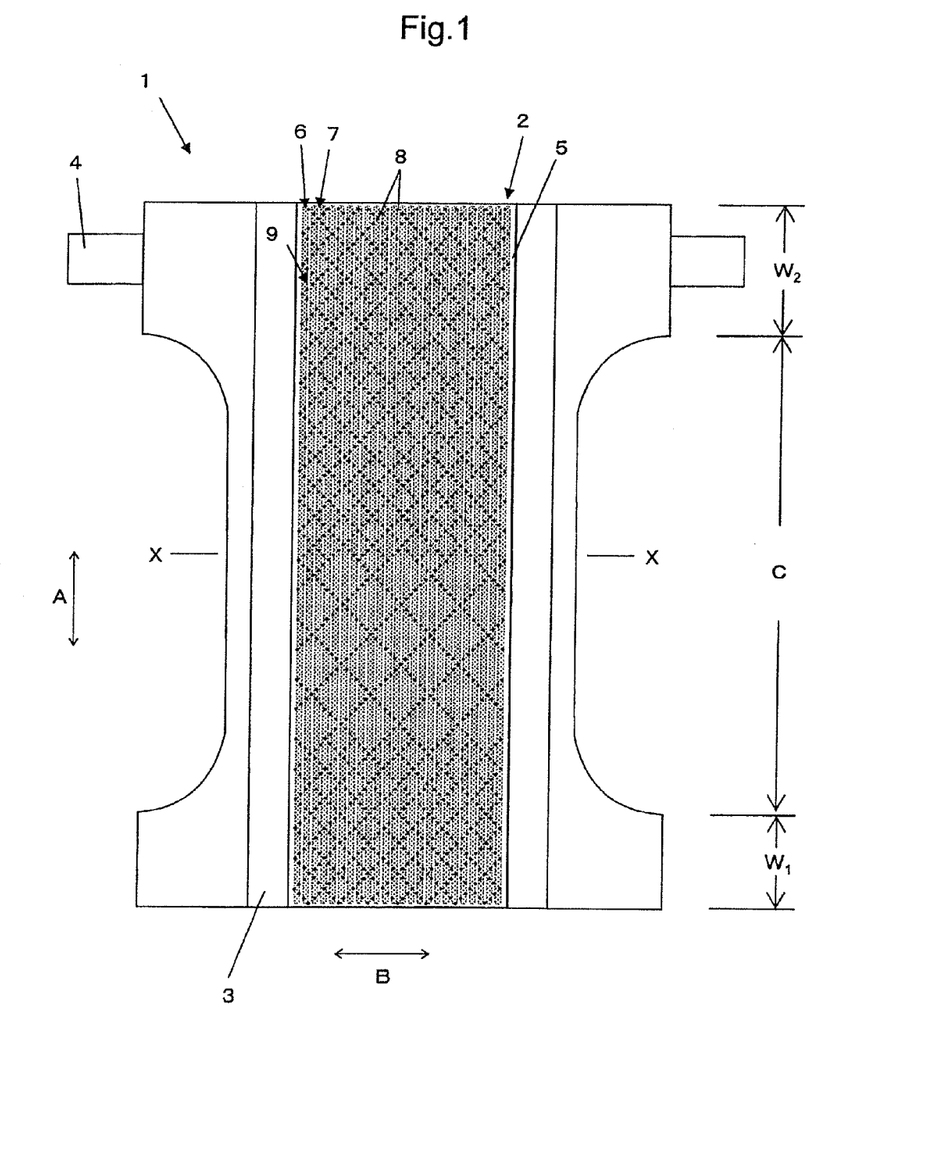
FIG. 1 is a plan view of a disposable diaper in accordance with an embodiment of the invention.

FIG. 1 is a plan view of a disposable diaper in accordance with an embodiment of the invention. The disposable diaper 1 shown in FIG. 1 comprises a liquid-permeable top sheet 2, a liquid-impermeable back sheet (not shown) and an absorber (not shown) between the top sheet 2 and the back sheet, and it has a front body waist region $W_1$, a crotch region C and a back body waist region $W_2$. The disposable diaper 1 shown in FIG. 1 also has an anti-leakage wall 3, and a tape fastener 4 attached to the back body waist region $W_2$.

The top sheet 2 is a nonwoven fabric having a plurality of ridges 6 and a plurality of recesses 7 on the skin contact surface 5 extending in the lengthwise direction A of the disposable diaper, and alternating in the widthwise direction B perpendicular to the lengthwise direction. In FIG. 1, the ridges 6 are represented as wave lines, and the dotted regions (stripe), and dots indicate that the dotted regions are raised above the sheet surface in non-dotted regions. The regions of the skin contact surface 5 that are not represented by wave lines and dots are the recesses 7.

The top sheet 2 also has point-like compressed sections (compressed spots, compressions) 8, formed by compressing of ridges 6 and/or recesses 7 on the front body waist region $W_1$ and/or back body waist region $W_2$, at a density in the range of 4.0-7.0/cm².

In the disposable diaper 1 shown in FIG. 1, zones of ridges 6 are present in the front body waist region $W_1$ and/or back body waist region $W_2$, sandwiched by two point-like compressed sections 8, and they have different heights than the adjacent ridges 6 at the same location in the lengthwise direction.

In the disposable diaper 1 shown in FIG. 1, the point-like compressed sections 8 have point-like compressed grooves (compressed spot line) 9 in the front body waist region $W_1$, the back body waist region $W_2$ and the waist region C, formed by continuous compressing of ridges 6 and/or recesses 7 at a fixed spacing.

As used herein, the term "density" used in relation to the point-like compressed sections means the number of point-like compressed sections per unit area of the top sheet, and it can be calculated by counting the number of point-like compressed sections within a prescribed area, such as 10 cm×10 cm of the nonwoven fabric, and dividing the counted value by the area.

Also as used herein, the term "crotch region" refers to the region that forms openings for passage of the legs of the wearer during use, the term "front body waist region" refers to the region that forms the front body in the waist region, being in front of the crotch region, and the term "back body waist region" refers to the region that forms the back body in the waist region, being behind the crotch region.

Figure 2:
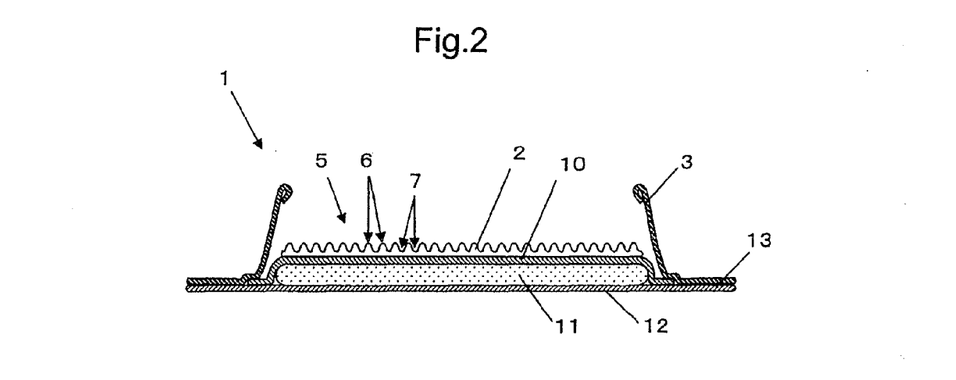
FIG. 2 is a cross-sectional view of the disposable diaper in FIG. 1, along cross-section line X-X.

FIG. 2 is a cross-sectional view of the disposable diaper in FIG. 1, along cross-section line X-X. The disposable diaper 1 shown in FIG. 2 comprises the liquid-permeable top sheet 2, a second sheet 10, a liquid-impermeable back sheet 12, an absorber 11 between the top sheet 2 and back sheet 12, and the anti-leakage wall 3. In the disposable diaper 1 shown in FIG. 2, the nonwoven fabric and back sheet 12 extending from the anti-leakage wall 3 form a side flap 13. The point-like compressed sections are not shown in FIG. 2. The second sheet 10 can be attached to the absorber 11 with known adhesives for example, hot melt adhesives, and the liquid-permeable top sheet 2 can be attached to the second sheet 10 with known adhesives for example, hot melt adhesives.

The disposable diaper 1 shown in FIG. 2 includes the second sheet 10, but the disposable diaper in accordance with further embodiments of the invention may omit such a second sheet.

Figure 3:
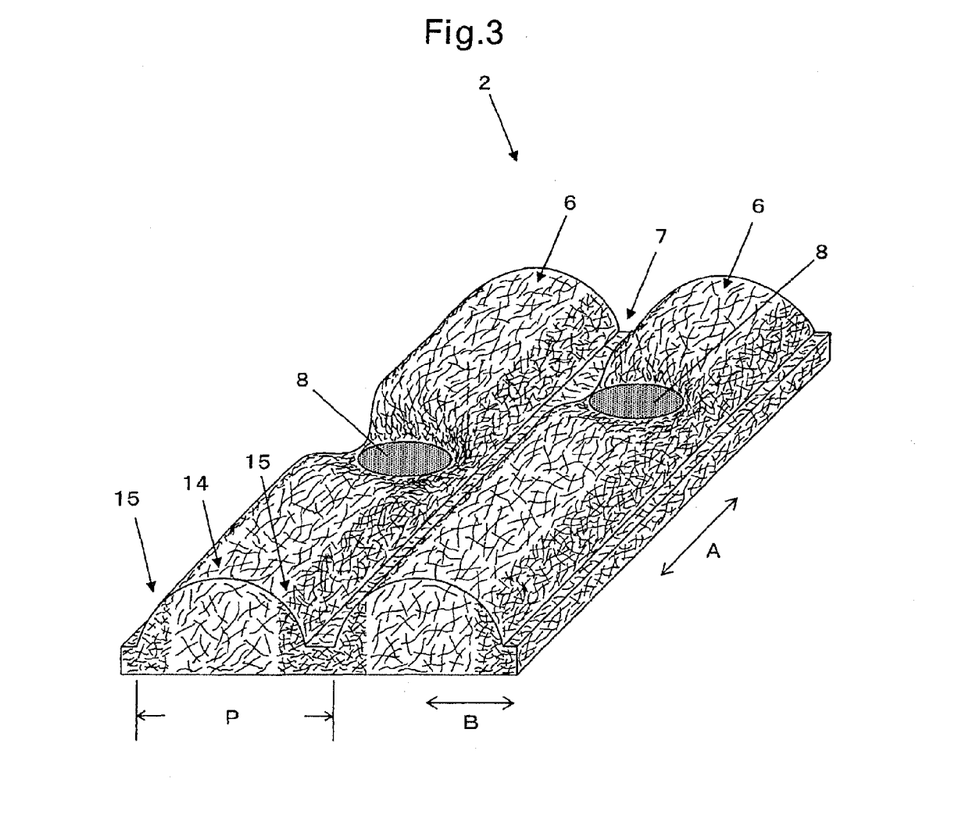
FIG. 3 is a magnified, perspective view of an area of the disposable diaper in FIG. 1, at areas around some point-like compressed sections.

FIG. 3 is a magnified perspective view of an area of the disposable diaper shown in FIG. 1 around some point-like compressed sections, showing only the top sheet for convenience of explanation. FIG. 3 shows two ridges 6 extending in parallel in the lengthwise direction A, and a recess 7 between the two ridges 6.

As shown in FIG. 3, the proportion of fibers oriented in the lengthwise direction A of the ridges 6 is higher than the proportion of fibers oriented in the lengthwise direction A of the recess 7. The point-like compressed sections 8 are formed by compressing of ridges 6.

In the top sheet 2 shown in FIG. 3, the fibers are orientated mainly in the lengthwise direction A at the center sections 14 and side sections 15 of the ridges 6, but in the peripheries of the point-like compressed sections 8, the fibers are depressed in the thickness direction i.e., in the direction of the absorber (not shown) which is under the top sheet 2. Consequently, moisture remaining on the skin can migrate through the center sections 14 and side sections 15 of the ridges 6 in the direction of the absorber (not shown), so that the top sheet used in the disposable diaper in accordance with embodiments of the invention exhibits an excellent absorber migration speed. As shown in FIG. 3, the point-like compressed sections, and especially the peripheries of the compressed sections, serve as migrating sections in which liquids migrate from a skin contactable side of the top sheet to the absorber. The effect of the migrating sections is increased when the point-like compressed sections are formed in the ridges, than when they are formed in the recesses.

Figure 4:
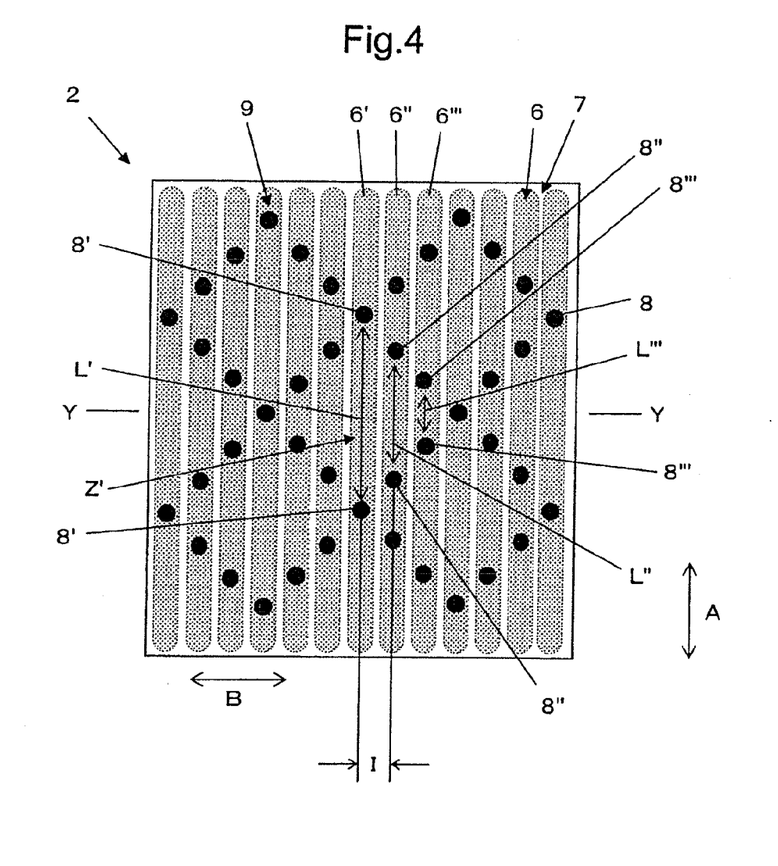
FIG. 4 is a diagram illustrating an arrangement of ridges and point-like compressed sections.
Figure 5:
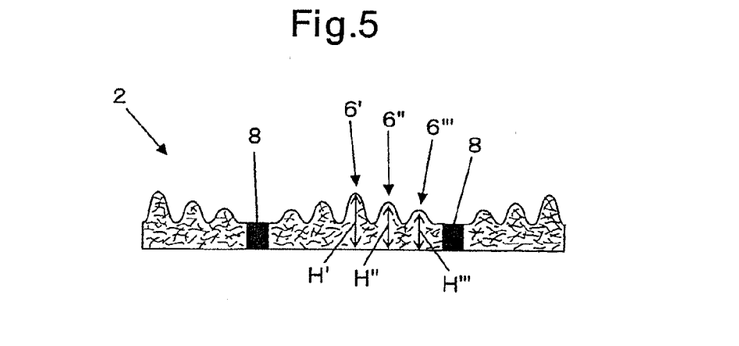
FIG. 5 is a cross-sectional view of FIG. 4 along cross-section line Y-Y and illustrating ridges of different heights at the same location in the lengthwise direction.

FIG. 4 is a diagram illustrating an arrangement of ridges and point-like compressed sections, while FIG. 5 is a cross-sectional view of FIG. 4 along the cross-section line Y-Y and illustrating ridges of different heights at the same location in the lengthwise direction. FIG. 4 and FIG. 5 show only the top sheet for convenience, and all of the point-like compressed sections 8 are formed on ridges 6, 6', 6" and 6'''. The top sheet 2 shown in FIG. 4 has a plurality of ridges 6 and a plurality of recesses 7 extending in the lengthwise direction A, and alternating in the widthwise direction B perpendicular to the lengthwise direction.

In FIG. 4, the ridges 6, 6', 6" and 6''' are represented as dotted regions (stripes), and the dots indicate that the dotted regions are raised above the sheet surface in non-dotted regions (recesses 7).

In the top sheet 2 shown in FIG. 4, the point-like compressed sections 8 are formed by continuous compressing of the ridges 6, 6', 6" and 6''' at a fixed spacing in zigzag fashions, and this forms point-like compressed grooves 9, the point-like compressed grooves 9 which are roughly linear or linear and crossing the lengthwise direction at an angle of 45°, while 4 point-like compressed grooves 9 form a side of a square in a lattice.

It should be noted that alternative patterns of the point-like compressed sections may be applied to the top sheet 2, as will be readily appreciated by those skilled in the art. The lattice pattern described herein is an exemplary pattern only.

In the top sheet 2 shown in FIG. 4, the ridge 6' in the zone Z' has a different height than the adjacent ridge 6" at the same location in the lengthwise direction.

In the top sheet 2 shown in FIG. 4, the distance between the two point-like compressed sections 8' on the ridge 6', in the lengthwise direction, is indicated as L'. Similarly, the distance between the two point-like compressed sections 8'" of the ridge 6", in the lengthwise direction, is indicated by L" and the distance between the two point-like compressed sections 8'" of the ridge 6'", in the lengthwise direction, is indicated as L'". As shown in FIG. 5, the heights of the ridges 6', 6" and 6'" at the centers of the two point-like compressed sections 8, 8', 8" and 8'" are indicated as H', H" and H'", respectively.

The relationship L'>L">L'" applies between the lengths L', L" and L'", while the relationship H'≥H"≥H'" applies between the heights H', H" and H'".

This is because, since the surrounding fibers are stretched during compressing of the ridges, a short spacing between two adjacent point-like compressed sections on the same ridge can result in stretching of the fibers at the ridges, and especially at the center sections of the ridges, thus lowering heights thereof. At a longer spacing (e.g., L') between two adjacent point-like compressed sections on the same ridge (e.g., 6'), the stretching effect is lower, and the height of the ridge (e.g., 6') between two adjacent point-like compressed sections is less reduced. At a shorter spacing (e.g., L'") between two adjacent compressed spots on the same ridge (e.g., 6'"), the stretching effect is greater, and the height of the ridge (e.g., 6'") between two adjacent point-like compressed sections is more reduced.

In the top sheet 2 shown in FIG. 4 and FIG. 5, the ridge 6' has the lowest height at the peripheries of the point-like compressed sections 8', as well as the highest height (height H') at the center section between the point-like compressed sections 8', which is the furthest distance from the compressions 8'. Similarly, the ridge 6" has the lowest height at the peripheries of the point-like compressed sections 8" and the furthest distance from the point-like compressed sections 8", as well as the highest height (height H") at the center section between the point-like compressed sections 8", which is the furthest distance from the compressions 8". The same applies for the ridges 6'" as well.

Thus, the adjacent ridge 6 and ridge 6' have different heights at the same location in the lengthwise direction. Also, the adjacent ridge 6' and ridge 6" have different heights at the same location in the lengthwise direction.

Thus, in the top sheet having ridges and recesses and point-like compressed sections as shown in FIG. 4, each ridge has a different height than the two adjacent ridges, i.e. the ridge 6" has a different height than the adjacent ridges 6' and 6'", at the same location in the lengthwise direction.

The relationship between the adjacent ridges is also satisfied when the point-like compressed sections are formed on both the ridges and recesses.

In the disposable diaper in accordance with some embodiments of the invention, the top sheet has ridges with different heights at the same locations in the lengthwise direction, so that the ridges with high heights allow the feeling during wear to be improved due to a better cushioning property and reduced skin contact area while the ridges with low heights, being closer to the migrating section, allow liquids in the top sheet to migrate to the absorber through the migrating section, thereby increasing the absorber migration speed.

In the disposable diaper 1 shown in FIG. 1, the top sheet has point-like compressed sections in all of the regions including the front body waist region, the crotch region and the back body waist region, but in the disposable diaper in accordance with some embodiments of the invention, the top sheet does not need to have point-like compressed sections in all of the regions including the front body waist region, crotch region and back body waist region.

Figure 6:
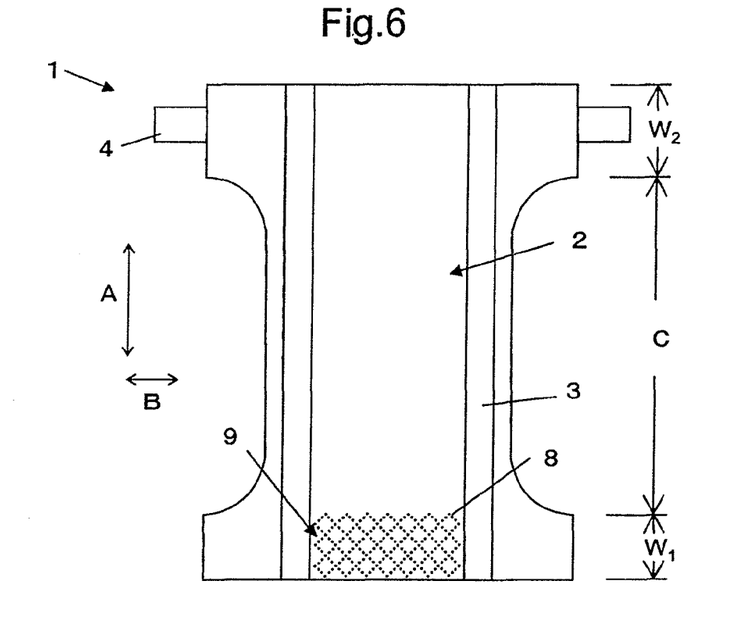
FIG. 6 is a plan view of a disposable diaper in accordance with an embodiment of the invention.

FIG. 6 is a plan view of a disposable diaper in accordance with an embodiment of the invention. The disposable diaper 1 shown in FIG. 6 comprises a liquid-permeable top sheet 2, a liquid-impermeable back sheet (not shown) and an absorber (not shown) between the top sheet 2 and the back sheet, and it has a front body waist region $W_1$, a crotch region C and a back body waist region $W_2$. The disposable diaper 1 shown in FIG. 6 also has an anti-leakage wall 3, and a tape fastener 4 attached to the back body waist region $W_2$. In FIG. 6, the ridges and recesses of the top sheet 2 are omitted for convenience.

The top sheet 2 shown in FIG. 6 has point-like compressed sections 8, formed by compressing of ridges and/or recesses (not shown) on the front body waist region $W_1$ only. In alternative arrangements, the point-like compressed sections may be formed in the back body waist region $W_2$ only. In either case, the point-like compressed sections 8 are preferably provided at a density in the range of about $6.2/cm^2$, however, may be provided at different densities. In the disposable diaper 1 shown in FIG. 6, the point-like compressed sections 8 also form point-like compressed grooves 9.

Although the top sheet 2 has point-like compressed sections 8 over the entire surface of the front body waist region $W_1$ (or the rear body waist region $W_2$) in the disposable diaper 1 shown in FIG. 6, according to another embodiment in accordance with an embodiment of the invention, the top sheet may have point-like compressed sections on only a part of the front body waist region $W_1$ (or the back body waist region $W_2$).

Figure 7:
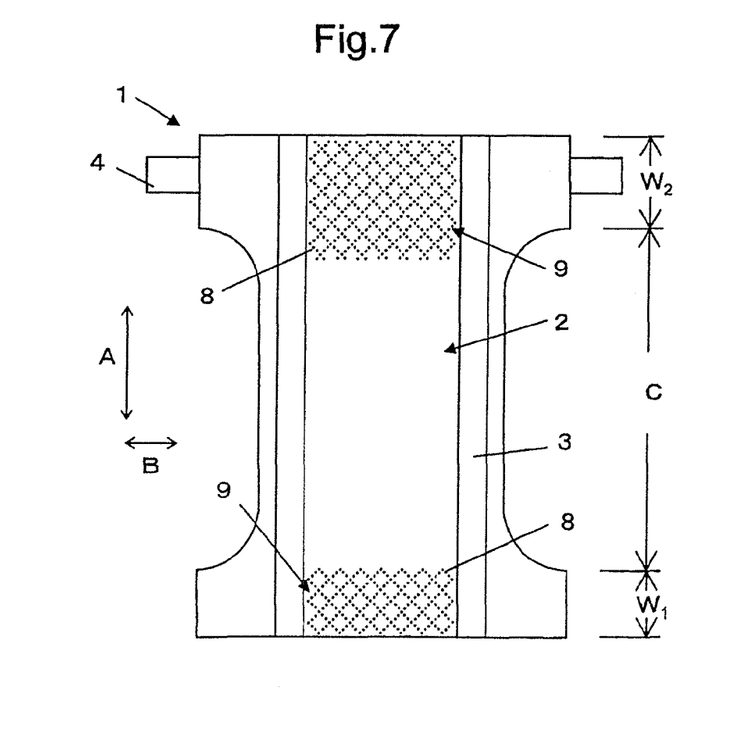
FIG. 7 is a plan view of a disposable diaper in accordance with an embodiment of the invention.

FIG. 7 is a plan view of a disposable diaper in accordance with an embodiment of the invention. The disposable diaper 1 shown in FIG. 7 has the same construction as FIG. 6, except for the point-like compressed sections 8.

The top sheet 2 shown in FIG. 7 has point-like compressed sections 8, formed by compressing of ridges and/or recesses (not shown) on the front body waist region $W_1$ and back body waist region $W_2$, at a density in the range of about preferably $6.2/cm^2$.

In the disposable diaper 1 shown in FIG. 7, the point-like compressed sections 8 also form point-like compressed grooves 9 in the front body waist region $W_1$ and the back body waist region $W_2$.

Although the top sheet 2 in the disposable diaper 1 shown in FIG. 7 has point-like compressed sections 8 over the entire surfaces of the front body waist region $W_1$ and the back body waist region $W_2$, according to another embodiment of the invention, the top sheet may have point-like compressed sections only on parts of the front body waist region and/or back body waist region.

In the disposable diaper 1 shown in FIG. 1, the density of the point-like compressed sections differs in different parts of the crotch region, but in the disposable diaper in accordance with some embodiments of the invention, the density of the point-like compressed sections may be the same in all of the regions including the front body waist region, crotch region and back body waist region.

Figure 8:
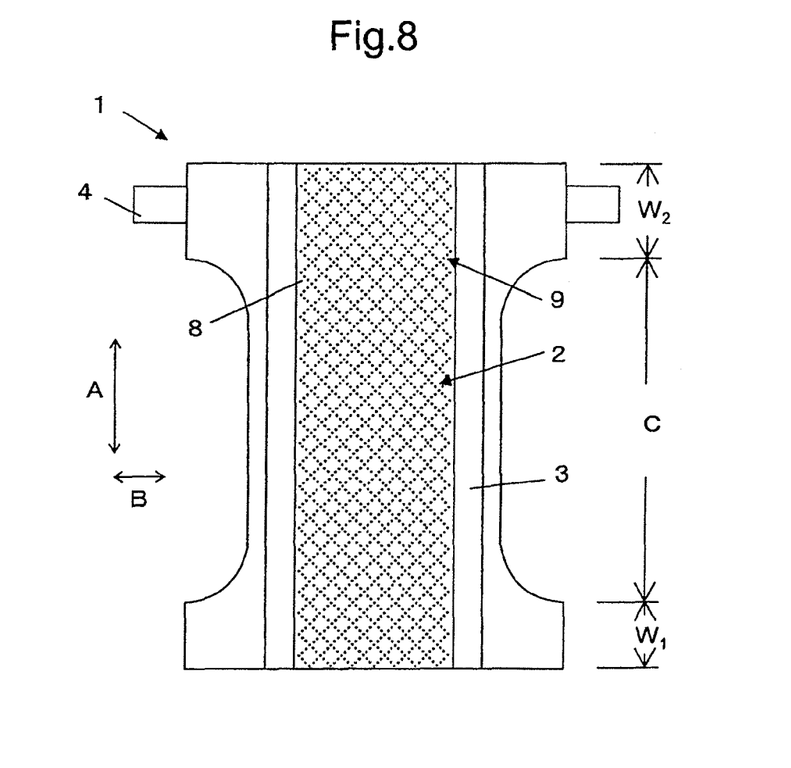
FIG. 8 is a plan view of a disposable diaper in accordance with an embodiment of the invention.

FIG. 8 is a plan view of a disposable diaper in accordance with an embodiment of the invention. The disposable diaper 1 shown in FIG. 8 has the same construction as FIG. 6, except for the point-like compressed sections 8.

The top sheet 2 shown in FIG. 8 has point-like compressed sections 8, formed by compressing of ridges and/or recesses (not shown) on the front body waist region $W_1$, the back body waist region $W_2$ and the crotch region C, at a density in the range of about preferably 6.2/cm².

In the disposable diaper 1 shown in FIG. 8, the point-like compressed sections 8 also form point-like compressed grooves 9.

Although the top sheet 2 in the disposable diaper 1 shown in FIG. 8 has point-like compressed sections 8 over the entire surfaces of the front body waist region $W_1$, the back body waist region $W_2$ and the crotch region C, according to another embodiment of the invention, the top sheet may have point-like compressed sections only on parts of the front body waist region $W_1$, back body waist region $W_2$ and/or crotch region C.

In the disposable diaper shown in FIG. 1, the point-like compressed sections are formed by continuous compressing of ridges and/or recesses at a fixed spacing, thereby forming roughly linear point-like compressed grooves, and preferably the roughly linear point-like compressed grooves are slanted with respect to the lengthwise direction at an angle θ (0°<θ≤90°, i.e., θ is greater than 0° and not greater than 90°.). When θ=0°, the point-like compressed grooves are parallel to the recesses and ridges, and therefore when the point-like compressed grooves and ridges overlap or the point-like compressed grooves and recesses overlap, the top sheet will not have ridges with various heights at the same location in the lengthwise direction, and therefore neither the feeling during wear nor the top sheet migration speed will be improved.

If the point-like compressed grooves are roughly linear, it will be possible to accomplish convenient and high-yield production of a nonwoven fabric with adjacent ridges having different heights than the adjacent ridges at the same location in the lengthwise direction, and to accomplish convenient and high-yield production of a nonwoven fabric with a suitable balance between feeling during wear, top sheet migration speed and absorber migration speed.

The point-like compressed grooves are preferably roughly linear, but as long as the top sheet has ridges with different heights it is not necessary for them to be linear, and for example, they may be in the form of roughly circular arcs, roughly elliptical arcs, zigzags, sine curves, or the like.

In the front body waist region, back body waist region and/or crotch region of the disposable diaper shown in FIG. 1, at least 4 point-like compressed grooves form a side of a closed figure, e.g., a square, in the lattice, and more specifically squares.

As used herein, the term "lattice" means a repeated pattern of shapes. Examples of such shapes include not only squares but also rectangular and rhomboid shapes.

If the point-like compressed grooves form a lattice, it will be possible to accomplish convenient and high-yield production of a nonwoven fabric with adjacent ridges having different heights than the adjacent ridges at the same location in the lengthwise direction, and to accomplish convenient and high-yield production of a nonwoven fabric with a suitable balance between feeling during wear, top sheet migration speed and absorber migration speed.

The shape formed by the point-like compressed grooves in the disposable diaper in accordance with an embodiment of the invention is/are not limited to squares, rectangles or rhomboids, so long as the top sheet has ridges with different heights, and for example, the shapes may be parallelograms, triangles, circles, ellipses or the like.

When the point-like compressed sections are present, their density in the front body waist region and back body waist region may be in the range of about 4.0 to about 7.0/cm², preferably in the range of about 5.0 to about 7.0/cm², and even more preferably in the range of about 6.0 to about 7.0/cm². A higher density increases the number of point-like compressed sections formed by compressing of the ridges and increases the migrating sections through which wiped moisture migrates to the absorber, and will therefore lead to a higher absorber migration speed. However, if the density is excessively increased the area of the compressed sections that are resistant to liquid permeation will be widened, thus tending to slow the top sheet migration speed.

In a disposable diaper, a portion of excreted fluid such as urine, that is not timely absorbed around the urination point of the crotch, can migrate into the front body waist region and/or back body waist region, being propagated on the skin of the wearer. In the front body waist region and/or back body waist region, therefore, preferably the absorber migration speed is increased over the top sheet migration speed which serves for treatment of large amounts of liquid, and the migrated liquid passes through the migrating section and migrates to the absorber.

Furthermore, since the front body waist region and/or back body waist region are also the sections where the disposable diaper is anchored to the wearer, the top sheet of the disposable diaper is usually in contact with the skin of the wearer. Consequently, these regions are regions of easy migration of the liquid to the top sheet, and it is desirable for the liquid that has migrated to the top sheet to further migrate to the absorber.

When the point-like compressed sections are present, their density is preferably no greater than about 4.0/cm² in the crotch region. In the crotch region, a large amount of urine is desirable to be momentarily absorbed and migrated to the top sheet, but a lower density will reduce the area of the compressed sections that are resistant to liquid permeation, and will thus increase the top sheet migration speed.

In consideration of ease of production, however, the density of the point-like compressed sections in the crotch region may be the same as the density of the point-like compressed sections in the front body waist region and/or back body waist region, i.e. in the range of 4.0-7.0/cm². This is because the top sheet migration speed will often be in an allowable range even with a density in the range of 4.0-7.0/cm².

The density can also be varied in the crotch region, depending on the location. For example, as shown in FIG. 1, the density of the point-like compressed sections in the crotch region may be lowered, to approximately 3.4/cm², for example, within the crotch region in a total range of 100 mm in the lengthwise direction from the urination point. This is because the urination point is the region which receives a large amount of urine during urination, and a high top sheet migration speed, i.e. a low density of point-like compressed sections, is preferred.

The area of each of the point-like compressed sections in the front body waist region, back body waist region and crotch region is preferably in the range of about 0.2 to about 9 mm², more preferably in the range of about 0.5 to about 4 mm², and even more preferably in the range of about 0.7 to about 2.0 mm². If the area is less than about 0.2 mm², compressing of the ridges may be insufficient with a thick nonwoven fabric, and if the area exceeds about 9 mm² the top sheet migration speed will tend to be lowered and the feeling during wear, including the feel on the skin, may be impaired.

The spacing of the point-like compressed sections in the front body waist region, back body waist region and crotch region is preferably in the range of about 2.0 to about 4.0 mm, and more preferably in the range of about 2.5 to about 3.5 mm. If the spacing is less than about 2.0 mm, the distance between point-like compressed sections will be shortened and liquids may not be retained. If the spacing is greater than about 4.0 mm, it may be required to increase the area of each to increase the density of the point-like compressed sections to achieve the desired migration speed.

As used herein, the term "spacing between point-like compressed sections" means the center-to-center distance between adjacent point-like compressed sections.

The ridges and recesses are also herein referred to as "irregularities." The pitch of irregularities in the front body waist region, back body waist region and crotch region is preferably from about 2.0 to about 6.5 mm, and more preferably from about 3.0 to about 5.0 mm. If the pitch is less than about 2.0 mm, the ridge heights will tend to be inadequate and the feeling during wear may be impaired. If the pitch is greater than about 6.5 mm, the spacing between ridges will tend to be too wide and the number of ridges will be reduced, resulting in an increased area in contact with the skin and impaired feeling during wear.

The pitch is the spacing between adjacent ridges, represented by "P" in FIG. 3.

The widths of the ridges in the front body waist region, back body waist region and crotch region are preferably in the range of about 1.5 to about 4.5 mm, more preferably in the range of about 2.0 to about 4.0 mm, and even more preferably in the range of about 2.5 to about 3.5 mm. If the width is greater than about 4.5 mm, the number of ridges per unit area will be reduced, resulting in an increased area in contact with the skin and impaired feeling during wear. If the width is less than about 1.5 mm, the ridge heights will tend to be inadequate.

The sum of the ridge widths and the recess widths is the pitch of irregularities.

The spacing of the point-like compressed sections in the widthwise direction preferably has a pitch which is the same as or shorter than that of the pitch of irregularities forming the ridges and recesses. This is because the point-like compressed sections may be formed only on the ridges, or the point-like compressed sections may be formed on different locations of the ridges and recesses.

As used herein, the spacing between point-like compressed sections in the widthwise direction is the distance "I" in FIG. 4, in the case of point-like compressed sections 8' and 8".

The heights of the ridges in the front body waist region, back body waist region and crotch region are preferably from about 0.5 to about 2.5 mm and more preferably from about 1.0 to about 2.0 mm. If the ridge heights are lower than about 0.5 mm, the feeling during wear will tend to be reduced, including a lower cushioning property and a reduced skin contact area. If the ridge heights are greater than about 2.0 mm, the distance between the surface of the top sheet and the absorber will be increased, tending to require more time for migration of the absorbed liquid into the absorber.

Figure 9:
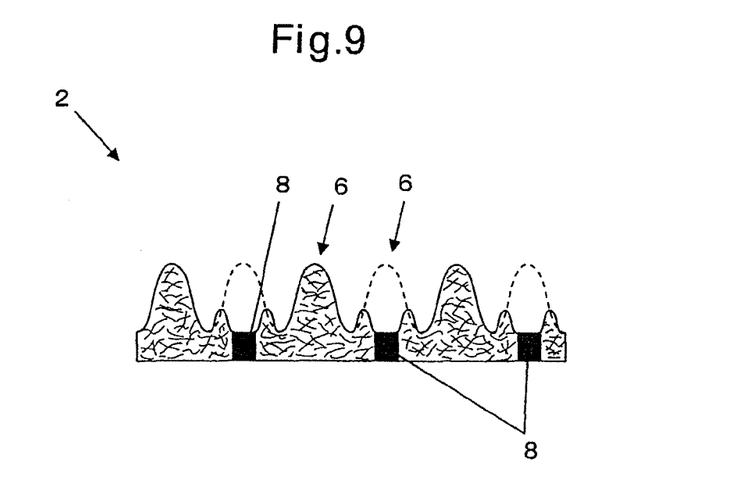
FIG. 9 is a cross-sectional view similar to FIG. 5 and illustrating an embodiment in which the widths of the point-like compressed sections in the widthwise direction are shorter than the widths of the ridges.

In the disposable diaper in accordance with some embodiments of the invention, the dimensions of the point-like compressed sections in the widthwise direction are preferably shorter than the widths of the ridges. As shown in FIG. 9, when the point-like compressed sections 8 have been formed at the center sections of the ridges 6, the original ridges 6 are eliminated and small ridges are formed around the peripheries of the point-like compressed sections 8, thus improving the feeling during wear and efficiently forming migrating sections, so that the absorber migration speed is increased. Furthermore, since this is related to a smaller area of the point-like compressed sections, the top sheet migration speed is increased.

In the disposable diaper in accordance with some embodiments of the invention, the proportion of fibers oriented in the lengthwise direction of the ridges is higher than the proportion of fibers oriented in the lengthwise direction of the recesses, and the orientation of fibers may be measured in the following manner. Measurement of the fiber orientation can be accomplished, for example, using a VHX-100 digital microscope by Keyence Corp.

(1) The top sheet is set on the observation stage with the skin contact surface facing upward and with the lengthwise direction in the longitudinal direction.

(2) The irregular fibers that have protruded forward are removed and the lens is focused onto the foremost fibers of the top sheet.

(3) The photographing depth is set to form a 3D image of the top sheet on a PC screen.

(4) The 3D image is converted to a 2D image.

(5) Several parallel lines periodically segmenting the lengthwise direction are drawn on the screen within the measurement range.

(6) In each cell fragmented by drawing of the parallel lines, it is observed whether the orientation of the fibers is in the lengthwise direction or the widthwise direction, and the number of fibers oriented in the lengthwise direction and widthwise direction are each counted.

(7) The proportion of fibers oriented in the lengthwise direction and widthwise direction is calculated.

As used herein, "fibers oriented in the lengthwise direction" means that they are oriented within a range from greater than $-45°$ to less than $+45°$ with respect to the lengthwise direction, and "fibers oriented in the widthwise direction" means that the fibers are oriented within a range from greater than $-45°$ to less than $+45°$ with respect to the widthwise direction.

A method for producing a disposable diaper in accordance with some embodiments of the invention will now be explained.

The nonwoven fabric having a plurality of recesses and ridges (also referred to as "nonwoven fabric with irregularities (undulations)") to be used as the top sheet in the disposable diaper in accordance with an embodiment of the invention, may be produced by a conventionally known method, such as the method described in Japanese Unexamined Patent Publication No. 2008-25081 (corresponding to U.S. Patent Application Publication No. 2009282660) or Japanese Unexamined Patent Publication No. 2008-25082 (corresponding to U.S. Patent Application Publication No. US 2008044628). The entire disclosures of all of the above listed applications are incorporated by reference herein.

Figure 10:
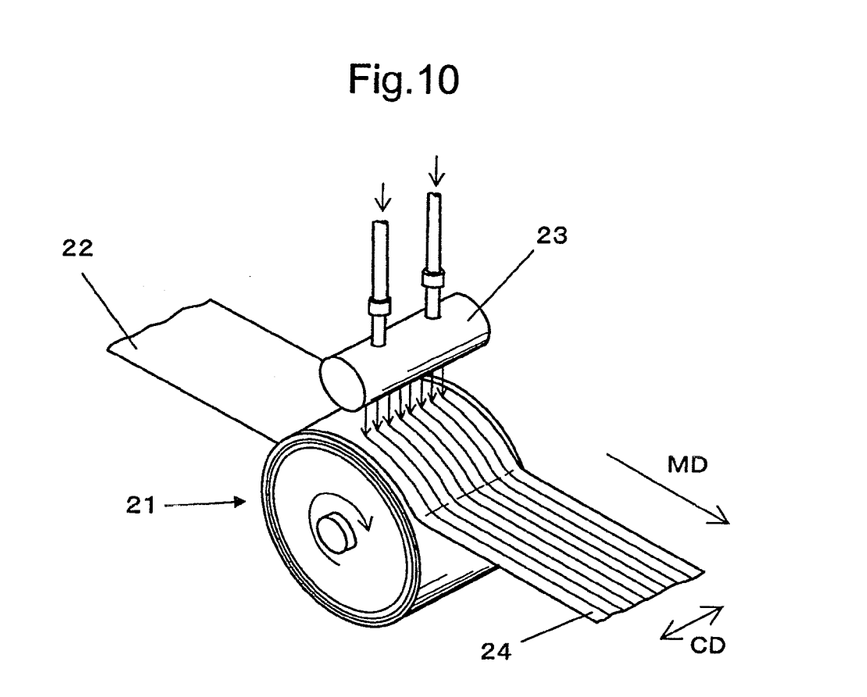
FIG. 10 is a diagram showing an exemplary method and equipment for producing a nonwoven fabric for use in a disposable diaper in accordance with an embodiment of the invention.

Specifically, as shown in FIG. 10 for example, a fiber web 22 may be placed on a roll having a supporting member 21 such as a mesh, and a fluid such as steam may be sprayed from fluid nozzles 23 onto the fiber web 22, to form a nonwoven fabric with irregularities 24. In the region of the nonwoven fabric with irregularities 24 which is directly under the nozzles through which the fluid is to be sprayed, the fibers are sorted in the cross direction CD that is perpendicular to the machine direction MD, forming recesses along the MD. The fibers collect in the region between each nozzle, forming ridges along the MD.

Figure 11:
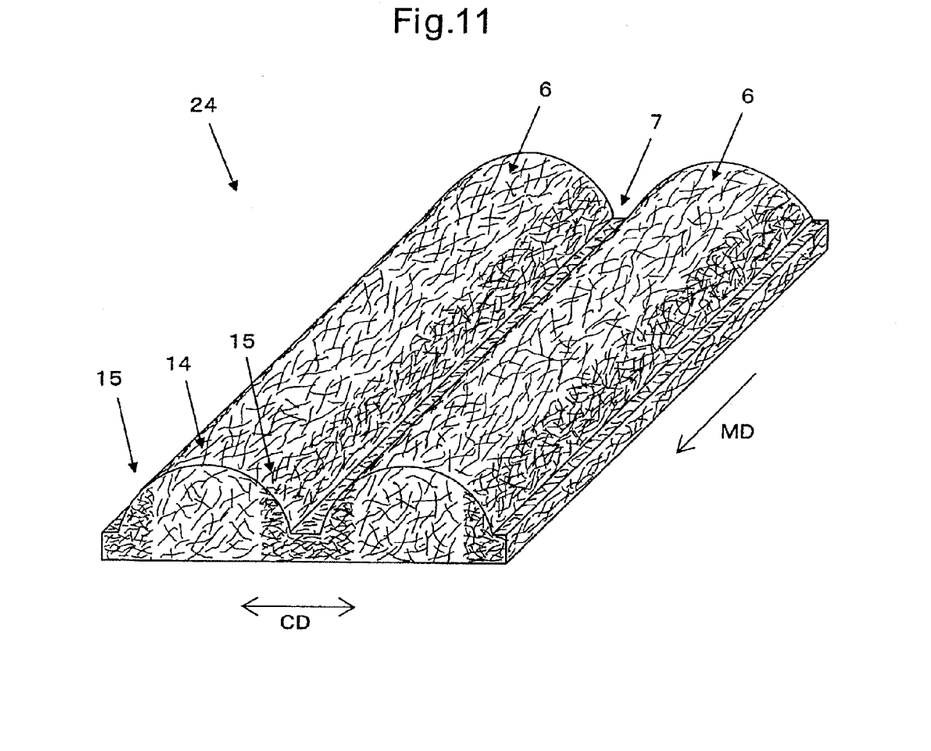
FIG. 11 is a diagram showing an exemplary nonwoven fabric having irregularities formed by the method and equipment illustrated in FIG. 10.

FIG. 11 is a diagram showing an exemplary nonwoven fabric having irregularities formed by the method and equipment illustrated in FIG. 10. In the nonwoven fabric with irregularities 24 shown in FIG. 11, the ridges 6 are formed along the MD, and recesses 7 are formed along the MD between the two ridges 6. At the center sections 14 and the side sections 15 on either side of the ridges 6, the fibers are oriented in the MD along the fluid flow.

The fluid may be steam, for example, with a spray volume of about 5-15 (nL/m$^2$), for example. Since a recess is formed in the nonwoven fabric directly under each fluid nozzle through which the fluid is blasted, with ridges being formed adjacent to the recesses, the fluid nozzle spacing may be designed so as to form the desired heights and widths of ridge, and pitch of irregularities.

There are no particular restrictions on the fibers in the fiber web and in the nonwoven fabric with irregularities formed from the fiber web, and for example, they may be polyethylene fibers, polyethylene terephthalate fibers, or combinations thereof.

The basis weight of the fiber web, and the average basis weight of the nonwoven fabric with irregularities formed from the fiber web, is preferably from about 10 to about 200 g/m$^2$, more preferably from about 20 to about 100 g/m$^2$, and even more preferably from about 20 to about 35 g/m$^2$. If the basis weight is less than about 10 g/m$^2$, the formed top sheet may tear during use. If the basis weight is greater than about 200 g/m$^2$, the thickness of the formed top sheet will be increased, tending to slow the top sheet migration speed of the disposable diaper in accordance with some embodiments of the invention.

The point-like compressed sections may be formed by any desired means known in the field, such as embossing. The embossing method is described in Japanese Unexamined Patent Publication Nos. 59-64043 (U.S. Pat. No. 4,518,451), 61-28002, and 57-69856. The point-like compressed sections are preferably solid and circular, as shown, but may take other forms, such as squares or otherwise, as will be readily appreciated by those skilled in the art.

The explanation in the present specification dealt with an open-type disposable diaper for the most part, but the disposable diaper in accordance with an embodiment of the invention encompasses not only open-type disposable diapers but also pants-type disposable diapers.

EXAMPLES

The invention will now be explained with examples, with the understanding that the invention is not meant to be limited to the examples.

Example 1

[Measurement of Top Sheet Migration Speed and Absorber Migration Speed]

The relationship between the density of the point-like compressed sections and the top sheet migration speed and absorber migration speed was examined.

Following the method described in Japanese Unexamined Patent Publication No. 2008-25082, there was prepared a nonwoven fabric with irregularities (basis weight: approximately 25 g/m$^2$, irregularity pitch: 4.0 mm, ridge width: 3.0 mm, recess width: 1.0 mm, ridge height: 1.0 mm) from a fiber web composed of polyethylene fibers and polyethylene terephthalate fibers (basis weight: approximately 25 g/m$^2$).

Top sheet Nos. 1-4 were produced by forming a square lattice of point-like compressed sections at varying density in the nonwoven fabric with irregularities, as shown in FIG. 8. The sizes of the square sides in the lattice formed by the point-like compressed grooves in the top sheet Nos. 1-4 were 6, 9, 12 and 18 mm, respectively. The point-like compressed sections in the top sheet Nos. 1-4 all had a dimension of 1 mm×1 mm squares, and the spacings between adjacent compressed spots along the same compressed spot line were all 2 mm.

A nonwoven fabric with irregularities having no point-like compressed sections was used as top sheet No. 5.

The top sheet migration speed and absorber migration speed were measured in the following manner. The absorber (absorbent core and sheet covering the core) was removed from a commercially available disposable diaper (Moony L Size, trade name of Unicharm Corp.), and the top sheet was fixed with a spiral hot-melt inserted on the skin side of the absorber, to form a sample.

The evaluation procedure was as follows.

(1) A cylinder (diameter: 60 mm, 55 g) was placed at the center of the absorbent core of the sample in the widthwise direction and lengthwise direction.

(2) A buret was used to drop 80 mL of artificial urine for 10 seconds from a height of 10 mm inside the cylinder.

(3) Upon completion of the dropping, measurement of the top sheet migration speed and absorber migration speed was initiated.

(4) The time required for the total amount of artificial urine in the cylinder to migrate into the top sheet of the sample after the dropping was completed was recorded as the "top sheet migration speed".

(5) The time required for the total amount of artificial urine in the cylinder to migrate into the absorber through the top sheet in the sample after the dropping was completed was recorded as the "absorber migration speed".

The artificial urine was prepared by adding 2 mass % urea, 0.8 mass % sodium chloride, 0.08 mass % magnesium sulfate heptahydrate, 0.03 mass % calcium chloride dihydrate and approximately 1 g of pigment: Blue #1, to ion-exchanged water.

The measurement was repeated 10 times, and the average value was used as the result.

The results are shown in Table 1.

The maximum height of the ridges (the height of the ridges at the center section of the lattice) was measured for the samples. The results are summarized in Table 1.

The ridge heights were measured in the following manner.

(1) The nonwoven fabric was cut using a HA-100B standard replacement blade for an HA-7NB Kokuyo cutter knife (trade name), to prepare a sample. Next, the sample was placed horizontally and a cross-sectional image was photographed at 25× magnification using a VHX-100 digital microscope by Keyence Corp.

(2) The cross-sectional image was processed with USB Digital image analysis software by Scalar Corp., to form a binary image. The threshold value was set to 50. The binary image was analyzed by selecting the "Hole filling" binary image shape analysis computing method, and then the object color "White" was selected for processing. Next, the "Hole filling" binary image shape analysis computing method was selected and the object color "Black" was selected for processing. The fibers exhibiting fluff, protruding from the fiber mass in the processed image, were removed to obtain an adjusted image without napping.

(3) In the adjusted image, the distances from the tops of the ridges to the horizontal plane on which the nonwoven fabric was placed were defined as the heights of the ridges.

(4) The distance from the bottoms of the recesses to the plane on which the nonwoven fabric was placed were defined as the heights of the recesses.

TABLE 1

| Top sheet | No. 1 | No. 2 | No. 3 | No. 4 | No. 5 |
|---|---|---|---|---|---|
| Lattice size (mm × mm) | 6 × 6 | 9 × 9 | 12 × 12 | 18 × 18 | — |
| Point-like compressed section density (/cm$^2$) | 8.33 | 6.17 | 4.86 | 3.40 | 0 |
| Top sheet migration speed (sec) | 10.2 | 9.7 | 9.5 | 8.3 | 7.9 |
| Absorber migration speed (sec) | 73 | 66 | 93 | 110 | 120 |
| Maximum ridge height (mm) | 0.5 | 0.6 | 0.8 | 0.9 | 1.0 |

Table 1 shows that a higher density of point-like compressed sections increases the absorber migration speed, while a lower density of point-like compressed sections increases the top sheet migration speed.

It also shows that varying the lattice size changes the maximum heights of the ridges. This suggests that varying the spacing between the point-like compressed sections on the same ridges in the lengthwise direction causes the heights of the same ridges to vary at different locations in the lengthwise direction.

This application claims the benefit of Japanese Application No. 2010-223115 the entire disclosure of which is incorporated by reference herein.

The present invention relates to the following aspects.

[Aspect 1]

A disposable diaper comprising a liquid-permeable top sheet, a liquid-impermeable back sheet and an absorber between the top sheet and back sheet, and having a front body waist region, a crotch region and a back body waist region, wherein the top sheet is a nonwoven fabric having on the skin contact surface a plurality of ridges and a plurality of recesses extending in the lengthwise direction of the disposable diaper, and alternating in the widthwise direction perpendicular to the lengthwise direction, the top sheet has point-like compressed sections, formed by compressing the ridges and/or recesses on the front body waist region and/or the back body waist region, at a density in the range of 4.0-7.0/cm$^2$, and zones of ridges are present in the front body waist region and/or the back body waist region, sandwiched by two point-like compressed sections, the ridges in those zones have different heights than the adjacent ridges at the same location in the lengthwise direction.

[Aspect 2]

The disposable diaper according to aspect 1, wherein the top sheet has point-like compressed sections in both the front body waist region and the back body waist region.

[Aspect 3]

The disposable diaper according to aspect 1 or 2, wherein the top sheet has point-like compressed sections formed by compressing ridges and/or recesses on the crotch region, at a density of no greater than 4.0/cm$^2$, and zones of ridges are present between two point-like compressed sections in the crotch region, the ridges in those zones have different heights than the adjacent ridges at the same location in the lengthwise direction.

[Aspect 4]

The disposable diaper according to any one of aspects 1 to 3, wherein the proportion of fibers oriented in the lengthwise direction of the ridges is higher than the proportion of fibers oriented in the lengthwise direction of the recesses.

[Aspect 5]

The disposable diaper according to any one of aspects 1 to 4, wherein the point-like compressed sections are formed by continuous compressing of ridges and/or recesses at a prescribed spacing, and create point-like compressed groove.

[Aspect 6]

The disposable diaper according to aspect 5, wherein the point-like compressed groove is roughly linear, and is crossing with the lengthwise direction at an angle of θ (0°<θ≤90°).

[Aspect 7]

The disposable diaper according to aspect 6, wherein a lattice is formed by a plurality of point-like compressed grooves.

[Aspect 8]

The disposable diaper according to aspect 6 or 7, wherein the spacing of the point-like compressed sections in the widthwise direction is equal to or shorter than the pitch of irregularities formed by the ridges and recesses.

[Aspect 9]

The disposable diaper according to any one of aspects 1 to 8, wherein the lengths of the point-like compressed sections in the widthwise direction are shorter than the widths of the ridges.

[Aspect 10]

The disposable diaper according to any one of aspects 1 to 8, wherein the ridges in the zones have different heights than their two adjacent ridges in the same location in the lengthwise direction.

[Aspect 11]

The disposable diaper according to any one of aspects 1 to 10, wherein the point-like compressed sections have areas in the range of 0.2-9 mm$^2$.

[Aspect 12]

The disposable diaper according to any one of aspects 1 to 11, wherein the spacings between the point-like compressed sections is in the range of 2.0-4.0 mm.

[Aspect 13]

The disposable diaper according to any one of aspects 1 to 12, wherein the point-like compressed sections are all formed by compressing of ridges.

The present invention is also defined by way of the following non-limiting features U1 to U16, and E1 to E15, which are not specific to the detailed embodiments described above.

[U1]

A disposable diaper, comprising a liquid-permeable top sheet, a liquid-impermeable back sheet and an absorber between the top sheet and back sheet, and having a front body waist region, a crotch region and a back body waist region, wherein the top sheet is a nonwoven fabric having on a skin contact surface thereof a plurality of ridges and a plurality of recesses extending in a lengthwise direction of the disposable diaper, and alternating in a widthwise direction perpendicular to the lengthwise direction, the top sheet has compressed spots, formed by compressing the ridges and/or recesses on the front body waist region and/or the back body waist region, at a density in the range of 4.0-7.0/cm$^2$, and zones of ridges are present in the front body waist region and/or the back body waist region, sandwiched by two compressed spots, the ridges in those zones have different heights than the adjacent ridges at the same location in the lengthwise direction.

[U2]

The disposable diaper according to U1, wherein the top sheet has compressed spots in both the front body waist region and the back body waist region.

[U3]

The disposable diaper according to U1 or U2, wherein the top sheet has compressed spots formed by compressing ridges and/or recesses on the crotch region, at a density of no greater than 4.0/cm², and zones of ridges are present between two compressed spots in the crotch region, the ridges in those zones have different heights than the adjacent ridges at the same location in the lengthwise direction.

[U4]

The disposable diaper according to any one of U1 to U3, wherein the proportion of fibers oriented in the lengthwise direction of the ridges is higher than the proportion of fibers oriented in the lengthwise direction of the recesses.

[U5]

The disposable diaper according to any one of U1 to U4, wherein the compressed spots are arranged at a fixed spacing along a plurality of compressed spot lines.

[U6]

The disposable diaper according to U5, wherein the compressed spot lines are roughly linear, and slanted with respect to the lengthwise direction at an angle of θ (0°<θ≤90°).

[U7]

The disposable diaper according to U6, wherein a lattice is formed by the plurality of compressed spot lines.

[U8]

The disposable diaper according to U6 or U7, wherein a spacing of the compressed spots in the widthwise direction is equal to or shorter than a pitch of irregularities formed by the ridges and recesses.

[U9]

The disposable diaper according to any one of U1 to U8, wherein dimensions of the compressed spots in the widthwise direction are shorter than widths of the ridges.

[U10]

The disposable diaper according to any one of U1 to U8, wherein each of the ridges in each of the zones has a different height than the two adjacent ridges in the same zone at the same location in the lengthwise direction.

[U11]

The disposable diaper according to any one of U1 to U10, wherein each of the compressed spots has an area in the range of 0.2-9 mm².

[U12]

The disposable diaper according to any one of U1 to U11, wherein the spacings between the compressed spots are in the range of 1-3 mm.

[U13]

The disposable diaper according to any one of U1 to U12, wherein the compressed spots are all formed on the ridges.

[U14]

The disposable diaper according to any one of U3 to U13, wherein the density of the compressed spots are different at different parts of the crotch region.

[U15]

The disposable diaper according to U14, wherein the density of the compressed spots in a range around a urination point in the crotch region is lower that other parts of the crotch region outside said range.

[U16]

The disposable diaper according to any one of U3 to U15, wherein the density of the compressed spots in the front body waist region and/or the back body waist region is higher than in a part of the crotch region to increase an absorber migration speed of the front body waist region and/or the back body waist region over a top sheet migration speed thereof.

[E1]

A nonwoven fabric having a lengthwise direction and a widthwise direction perpendicular to the lengthwise direction and being provided on its surface with a plurality of ridges and a plurality of recesses extending in the lengthwise direction, and alternating in the widthwise direction, the fabric has a plurality of point-like compressions, formed by compressing the ridges and/or recesses, the compressions being provided at a density in the range of 4.0-7.0/cm² in one or more areas on the sheet's surface, wherein zones of the ridges between adjacent compressions have different heights than the adjacent ridges at the same location in the lengthwise direction.

[E2]

The nonwoven fabric according to E1, wherein immediately adjacent compressions in the widthwise direction are offset from one another in the lengthwise direction.

[E3]

The nonwoven fabric according to E1 or E2 wherein the compressions are arranged in a plurality of lines that extend in the lengthwise direction and are spaced from one another in the widthwise direction, the compressions of each line are spaced from one another in the lengthwise direction and aligned with one another in the widthwise direction, a zone is formed between each immediately adjacent pair of compressions of each line, and wherein immediately adjacent zones in the widthwise direction have different lengths in the lengthwise direction.

[E4]

The nonwoven fabric according to E1, E2 or E3, wherein the proportion of fibers oriented in the lengthwise direction in the ridges is higher than the proportion of fibers oriented in the lengthwise direction in the recesses.

[E5]

The nonwoven fabric according to any one of E1 to E4, wherein the compressions are formed in lines of evenly spaced compressions that cross with the lengthwise direction at an oblique angle.

[E6]

The disposable diaper according to E5, wherein a lattice pattern is formed by the lines of compressions.

[E7]

The disposable diaper according to any one of E1 to E6, wherein the spacing of the point-like compressed sections in the widthwise direction is equal to or shorter than the pitch of undulations formed by the ridges and recesses.

[E8]

The disposable diaper according to any one of E1 to E7, wherein the compressions are narrower than the ridges in the widthwise direction.

[E9]

The disposable diaper according to any one of E1 to E8, wherein the ridges in the zones have different heights than their immediately adjacent ridges in the same location in the lengthwise direction.

[E10]

The disposable diaper according to any one of E1 to E9, wherein the compressions have areas in the range of 0.2-9 mm².

[E11]

The disposable diaper according to any one of E1 to E10, wherein the spacings between the compressions are in the range of 1-3 mm.

[E12]

The disposable diaper according to any one of E1 to E11, wherein the compressions are all provided on the ridges.

[E13]

A disposable diaper comprising a liquid-permeable top sheet, a liquid-impermeable back sheet and an absorber between the top sheet and back sheet, and having a front body waist region, a crotch region and a back body waist region, wherein the top sheet comprises the nonwoven fabric according to any preceding claim, which is formed with the plurality of ridges and recesses on its skin contact surface.

[E14]

The disposable diaper according to E13, wherein the top sheet has compressions in both the front body waist region and the back body waist region.

[E15]

The disposable diaper according to E13 or E14, wherein the top sheet has point-like compressed sections formed by compressing ridges and/or recesses on the crotch region, at a density of no greater than 4.0/cm$^2$ and zones of ridges are present between two point-like compressed sections in the crotch region, the ridges in those zones have different heights than the adjacent ridges at the same location in the lengthwise direction.

The aspects of the present invention described above may be arranged in at least the following items:

A nonwoven fabric having a lengthwise direction and a widthwise direction perpendicular to the lengthwise direction and being provided on its surface with a plurality of ridges and a plurality of recesses extending in the lengthwise direction, and alternating in the widthwise direction, the fabric has a plurality of point-like compressions, formed by compressing the ridges and/or recesses, the compressions being provided at a density in the range of 4.0-7.0/cm$^2$ in one or more areas on the sheet's surface, wherein zones of the ridges between adjacent compressions have different heights than the adjacent ridges at the same location in the lengthwise direction.

A disposable diaper comprising a liquid-permeable top sheet, a liquid-impermeable back sheet and an absorber between the top sheet and back sheet, and having a front body waist region, a crotch region and a back body waist region, wherein the top sheet comprises the nonwoven fabric according to the preceding paragraph, which is formed with the plurality of ridges and recesses on its skin contact surface.

Additionally, the present invention may include the following embodiments:

The nonwoven fabric is preferably thinner in the zones. In particular, the nonwoven fabric may be thinner in the zones than in regions of the absorbent layer which do not feature the compressions.

The compressions may be provided in one or more discrete regions of the fabric or may be provided over the entire surface of the nonwoven fabric. Different regions of the surface of the nonwoven fabric may have different densities of compressions.

The compressions may all be provided on the ridges. In this case the adjacent compressions defining the zones may be immediately adjacent compressions in the lengthwise direction which are located on the same ridge.

Immediately adjacent compressions in the widthwise direction are preferably offset from one another in the lengthwise direction.

The compressions may be arranged in a plurality of lines that extend in the lengthwise direction and are spaced from one another in the widthwise direction, the compressions of each line are spaced from one another in the lengthwise direction and aligned with one another in the widthwise direction, a zone is formed between each immediately adjacent pair of compressions of each line, and wherein immediately adjacent zones in the widthwise direction have different lengths in the lengthwise direction.

The height of the zones may be measured at a mid-point between the adjacent compressions.

The proportion of fibers oriented in the lengthwise direction in the ridges may be higher than the proportion of fibers oriented in the lengthwise direction in the recesses.

The compressions may be formed in lines of evenly spaced compressions that cross with the lengthwise direction at an oblique angle. A lattice pattern may be formed by the lines of compressions.

The spacing of the point-like compressed sections in the widthwise direction may be equal to or shorter than the pitch of undulations formed by the ridges and recesses.

The compressions may be narrower than the ridges in the widthwise direction.

The ridges in the zones may have different heights than their immediately adjacent ridges in the same location in the lengthwise direction.

The basis weight of the fiber web, and the average basis weight of the nonwoven fabric with irregularities formed from the fiber web, may be 10 to 200 g/m$^2$. More preferably it is 20 to 100 g/m$^2$. Most preferably it is 20 to about 35 g/m$^2$.

The heights of the ridges may be 0.5 to about 2.5 mm. Most preferably 1.0 to 2.0 mm.

The widths of the ridges may be 1.5 to 4.5 mm. More preferably 2.0 to 4.0 mm, and most preferably 2.5 to 3.5 mm.

The pitch of undulations forming the ridges and recesses may be 2.0 to 6.5 mm. Most preferably from 3.0 to 5.0 mm.

The compressions may have areas in the range of 0.2-9 mm$^2$. The compressions are preferably solid embossments. The compressions may be circular or square.

The spacings between the compressions may be in the range of 1-3 mm. Most preferably in the range of 1.5 to 2.5 mm In the disposable diaper the top sheet may have compressions in both the front body waist region and the back body waist region. The compressions may be provided in only the front and/or back body waist regions.

In the disposable diaper the top sheet may have point-like compressed sections formed by compressing ridges and/or recesses on the crotch region, at a density of no greater than 4.0/cm2 and zones of ridges with reduced height may be present between every two point-like compressed sections in the crotch region, the ridges in those zones have different heights than the adjacent ridges at the same location in the lengthwise direction.

REFERENCES SIGNS LIST

1 Disposable diaper
2 Top sheet
3 Anti-leakage wall
4 Tape fastener
5 Skin contact surface
6, 6', 6", 6''' Ridges
7 Recess
8 Point-like compressed section
9 Point-like compressed groove
10 Second sheet
11 Absorber
12 Back sheet
13 Side flap
14 Center section
15 Side section
21 Supporting member
22 Fiber web
23 Fluid nozzle
24 Nonwoven fabric with irregularities
A Lengthwise direction
B Widthwise direction I Spacing between point-like compressed sections in widthwise direction
P Pitch
MD Machine direction
CD Cross direction
$W_1$ Front body waist region
$W_2$ Back body waist region
C Crotch region
Z' Zone

The invention claimed is:

1. A disposable diaper comprising a liquid-permeable top sheet, a liquid-impermeable back sheet and an absorber between the top sheet and back sheet, and having a front body waist region, a crotch region and a back body waist region,
wherein the top sheet is a nonwoven fabric having on the skin contact surface a plurality of ridges and a plurality of recesses extending in the lengthwise direction of the disposable diaper, and alternating in the widthwise direction perpendicular to the lengthwise direction,
the top sheet has point-like compressed sections, formed by compressing the ridges and/or recesses on the front body waist region and/or the back body waist region, at a density in the range of $4.0\text{-}7.0/\text{cm}^2$, and
zones of ridges are present in the front body waist region and/or the back body waist region, sandwiched by two point-like compressed sections, the ridges in those zones have different heights than the adjacent ridges at the same location in the lengthwise direction.

2. The disposable diaper according to claim 1, wherein the top sheet has point-like compressed sections in both the front body waist region and the back body waist region.

3. The disposable diaper according to claim 1, wherein the top sheet has point-like compressed sections formed by compressing ridges and/or recesses on the crotch region, at a density of no greater than $4.0/\text{cm}^2$ and zones of ridges are present between two point-like compressed sections in the crotch region, the ridges in those zones have different heights than the adjacent ridges at the same location in the lengthwise direction.

4. The disposable diaper according to claim 1, wherein the proportion of fibers oriented in the lengthwise direction of the ridges is higher than the proportion of fibers oriented in the lengthwise direction of the recesses.

5. The disposable diaper according to claim 1, wherein the point-like compressed sections are formed by continuous compressing of ridges and/or recesses at a fixed spacing, and create a point-like compressed groove.

6. The disposable diaper according to claim 5, wherein the point-like compressed groove is roughly linear, and is crossing with the lengthwise direction at an angle of $\theta(0°<\theta\leq90°)$.

7. The disposable diaper according to claim 6, wherein a lattice is formed by a plurality of point-like compressed grooves.

8. The disposable diaper according to claim 6, wherein the spacing of the point-like compressed sections in the widthwise direction is equal to or shorter than the pitch of irregularities formed by the ridges and recesses.

9. The disposable diaper according to claim 1, wherein the lengths of the point-like compressed sections in the widthwise direction are shorter than the widths of the ridges.

10. The disposable diaper according to claim 1, wherein the ridges in the zones have different heights than their two adjacent ridges in the same location in the lengthwise direction.

11. The disposable diaper according to claim 1, wherein the point-like compressed sections have areas in the range of $0.2\text{-}9\text{ mm}^2$.

12. The disposable diaper according to claim 1, wherein the spacings between the point-like compressed sections are in the range of 2.0-4.0 mm.

13. The disposable diaper according to claim 1, wherein the point-like compressed sections are all formed by compressing of ridges.

14. The disposable diaper according to claim 1, wherein the ridges in the zones of ridges have different distances between the two point-like compressed sections of the ridge than those of the adjacent ridges.

15. The disposable diaper according to claim 1, wherein the point-like compressed sections are point compressed sections.

16. The disposable diaper according to claim 1, wherein the point-like compressed sections are circular compressed sections.

17. The disposable diaper according to claim 1, wherein the point-like compressed sections are compressed sections within the boundaries of respective ridges.

18. A disposable diaper comprising a liquid-permeable top sheet, a liquid-impermeable back sheet and an absorber between the top sheet and back sheet, and having a front body waist region, a crotch region and a back body waist region,
wherein the top sheet is a nonwoven fabric having on the skin contact surface a plurality of ridges and a plurality of recesses extending in the lengthwise direction of the disposable diaper, and alternating in the widthwise direction perpendicular to the lengthwise direction,
the top sheet has compressed sections having a diameter that is within the diameter of the ridges normal to the lengthwise direction of the ridges, formed by compressing the ridges and/or recesses on the front body waist region and/or the back body waist region, at a density in the range of $4.0\text{-}7.0/\text{cm}^2$, and
zones of ridges are present in the front body waist region and/or the back body waist region, sandwiched by two point-like compressed sections, the ridges in those zones have different heights than the adjacent ridges at the same location in the lengthwise direction.

19. The disposable diaper according to claim 18, wherein the compressed sections are point compressed sections.

20. The disposable diaper according to claim 18, wherein the compressed sections are circular compressed sections.

21. The disposable diaper according to claim 18, wherein the ridges in the zones of ridges have different distances between the two point-like compressed sections of the ridge than those of the adjacent ridges.

* * * * *